United States Patent
Claus (10) Patent No.: US 8,000,522 B2
(45) Date of Patent: Aug. 16, 2011

(54) METHOD AND SYSTEM FOR THREE-DIMENSIONAL IMAGING IN A NON-CALIBRATED GEOMETRY

(75) Inventor: Bernhard Erich Hermann Claus, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1231 days.

(21) Appl. No.: 11/701,760

(22) Filed: Feb. 2, 2007

(65) Prior Publication Data
US 2008/0186311 A1   Aug. 7, 2008

(51) Int. Cl.
*G06K 9/00* (2006.01)
(52) U.S. Cl. .................... 382/154; 382/131
(58) Field of Classification Search .......... 382/128–131, 382/154; 345/419; 378/4, 205
See application file for complete search history.

(56) References Cited

U.S. PATENT DOCUMENTS

| | | | |
|---|---|---|---|
| 5,442,674 A | 8/1995 | Picard et al. | |
| 6,081,577 A | 6/2000 | Webber | |
| 6,139,183 A * | 10/2000 | Graumann | 378/206 |
| 6,289,235 B1 | 9/2001 | Webber | |
| 6,379,041 B1 * | 4/2002 | Schuetz et al. | 378/205 |
| 6,491,430 B1 | 12/2002 | Seissler | |
| 6,549,607 B1 | 4/2003 | Webber | |
| 6,666,579 B2 * | 12/2003 | Jensen | 378/197 |
| 6,754,298 B2 * | 6/2004 | Fessler | 378/4 |
| 6,801,597 B2 | 10/2004 | Webber | |
| 6,810,278 B2 | 10/2004 | Webber | |
| 7,110,807 B2 | 9/2006 | Webber | |
| 7,536,040 B2 * | 5/2009 | Hornegger et al. | 382/128 |
| 2003/0058999 A1 | 3/2003 | Mitschke | |
| 2003/0072417 A1 | 4/2003 | Kaufhold | |
| 2003/0194121 A1 * | 10/2003 | Eberhard et al. | 382/132 |
| 2005/0094771 A1 | 5/2005 | Basu et al. | |
| 2007/0052700 A1 * | 3/2007 | Wheeler et al. | 345/419 |
| 2007/0122020 A1 | 5/2007 | Claus et al. | |

FOREIGN PATENT DOCUMENTS

DE   19936408   3/2001

OTHER PUBLICATIONS

Stevens "Volumetric Tomographic Imaging", Stanford University, Dec. 2000, pp. 22-58.*
Webber et al., Synthesis of Arbitrary X-Ray Projections from a Finite Number of Existing Projections, SPIE, vol. 535, 1985, p. 84-91.

(Continued)

*Primary Examiner* — Daniel G Mariam
(74) *Attorney, Agent, or Firm* — Fletcher Yoder (57) ABSTRACT

A technique is provided for three-dimensional imaging in a non-calibrated geometry. In one embodiment, the technique includes acquiring a plurality of projection images through an imaging volume; estimating an imaging geometry using at least one of fiducial markers or anatomical features represented in the projection images; and reconstructing a configurable volumetric representation of some or all of the imaging volume using the estimated imaging geometry, wherein the act of reconstructing accounts for one or more geometry dependent factors. In addition, a system is provided which includes a computer configured to estimate an imaging geometry using at least one of fiducial markers or anatomical features represented in a plurality of projection images acquired through an imaging volume and to reconstruct a configurable volumetric representation of some or all of the imaging volume using the estimated imaging geometry, wherein the act of reconstructing accounts for one or more geometry dependent factors.

23 Claims, 3 Drawing Sheets

OTHER PUBLICATIONS

Webber et al., Tuned-Aperture Computer Technology (TACT TM). Theory and application for three-dimensional dento-alveolar imaging, Dentomaxillofacial Radiology (1997) 26, pp. 53-62.

Sonka, M., et al.; "Handbook of Medical Imaging. vol. 2: Medical Image Processing and Analysis", Jan. 1, 2000, Chapter 17, pp. 1061-1129.

* cited by examiner

METHOD AND SYSTEM FOR THREE-DIMENSIONAL IMAGING IN A NON-CALIBRATED GEOMETRY

BACKGROUND

The present invention relates generally to the field of medical imaging, and more specifically to the field of imaging geometry calibration and reconstruction. In particular, the present invention relates to three-dimensional imaging in a non-calibrated geometry.

Volumetric imaging devices are widely used in both medical and non-medical imaging fields. For example, various modalities serve to generate image data based upon specific physical properties of materials and their interaction with imaging systems. Such modalities include computed tomography (CT) systems, X-ray systems, magnetic resonance imaging (MRI) systems, positron emission tomography (PET) systems, ultrasound systems, and so forth. These systems are generally designed to collect image data in response to various radiation, stimuli, or signal sources emitted by or transmitted through a subject. The signals can then be filtered and manipulated to form a dataset from which a reconstructed image may be generated. It should be noted that while reference is made throughout the present discussion to modalities employed in the medical imaging field, these same and other modalities may be employed in a wide range of other fields, including baggage processing, human and non-human screening, industrial quality control, manufacturing monitoring, seismography, meteorology, and so forth.

A simple X-ray imaging technique may involve generating X-rays using an X-ray tube or other X-ray source and directing the X-rays through an imaging volume in which the part of the patient to be imaged is located. As the X-rays pass through the patient, the X-rays are attenuated based on the composition of the tissue they pass through. The attenuated X-rays then impact a detector that converts the X-rays into signals that can be processed to generate an image of the part of the patient through which the X-rays passed based on the attenuation of the X-rays. Three-dimensional information may be obtained by acquiring additional images at different viewing angles relative to the imaging volume. The angularly displaced images acquired in this manner may then be reconstructed to produce a three-dimensional representation of the imaging volume including internal structures, which may be displayed on a monitor, printed to a printer, or reproduced on film. A technologist or clinician may then review the three-dimensional representation, such as to detect clinically significant irregularities or abnormalities or to assess the three-dimensional landscape prior to an invasive or non-invasive medical procedure. The reconstructed volumetric dataset may also be used for further processing, such as, for example, computer assisted detection and/or diagnosis (CAD).

In order to generate an accurately reconstructed three-dimensional image from the data produced by the various modalities discussed above, it is important to know the imaging geometry accurately. That is, the positions of the source, detector, and imaged volume relative to one another must be accurately known in order to determine how to properly reconstruct and/or combine the data to generate a true representation of the imaged volume. For example, in some imaging modalities, such as C-arm systems and tomosynthesis, the imaging geometry may change with each new data acquisition.

Currently, an imaging system must be calibrated in order to accurately reconstruct three-dimensional images from data obtained on the system. This calibration may include measuring the distances and angles between the elements of the system or imaging using one or more calibration phantoms. Measuring system components can be time-consuming and is not always accurate enough to produce good results. Calibration using appropriate phantoms may be more accurate than simply measuring the imaging system, however this technique may be limited to systems in which the imaging geometry is consistent and repeatable. In some cases, the system simply cannot be calibrated before a subject is imaged. For example, the position or trajectory of the imaging system may be determined in real-time as a function of patient anatomy or other factors, or the mechanical or motion control tolerances of the system may not be sufficiently accurate.

Therefore, it would be advantageous to have a method for determining the imaging geometry and reconstructing a volumetric image in a three-dimensional imaging system where prior calibration of the imaging system is not possible or is not practical.

BRIEF DESCRIPTION

There is provided a method for three-dimensional imaging in a non-calibrated geometry including acquiring a plurality of projection images through an imaging volume; estimating an imaging geometry using at least one of fiducial markers or anatomical features represented in the projection images; and reconstructing a configurable volumetric representation of some or all of the imaging volume using the estimated imaging geometry, wherein the act of reconstructing accounts for one or more geometry dependent factors.

There is further provided a method for three-dimensional imaging in a non-calibrated geometry including acquiring a plurality of projection images through an imaging volume; estimating an imaging geometry using one or more anatomical features represented in the projection images; and reconstructing a volumetric representation of some or all of the imaging volume using the established imaging geometry.

There is further provided an image processing system including a computer, wherein the computer is configured to estimate an imaging geometry using at least one of fiducial markers or anatomical features represented in a plurality of projection images acquired through an imaging volume and to reconstruct a configurable volumetric representation of some or all of the imaging volume using the estimated imaging geometry, wherein the act of reconstructing accounts for one or more geometry dependent factors.

There is further provided an image processing system including a computer, wherein the computer is configured to estimate an imaging geometry using anatomical features represented in a plurality of projection images acquired through an imaging volume and to reconstruct a volumetric representation of some or all of the imaging volume using the estimated imaging geometry.

There is further provided one or more tangible, machine readable media, including code executable to perform the acts of estimating an imaging geometry using at least one of fiducial markers or anatomical features represented in a plurality of projection images acquired through an imaging volume and reconstructing a configurable volumetric representation of some or all of the imaging volume using the estimated imaging geometry, wherein the act of reconstructing accounts for one or more geometry dependent factors.

There is further provided one or more tangible, machine readable media, including code executable to perform the acts of estimating an imaging geometry using anatomical features represented in a plurality of projection images acquired through an imaging volume and reconstructing a volumetric representation of some or all of the imaging volume using the estimated imaging geometry.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
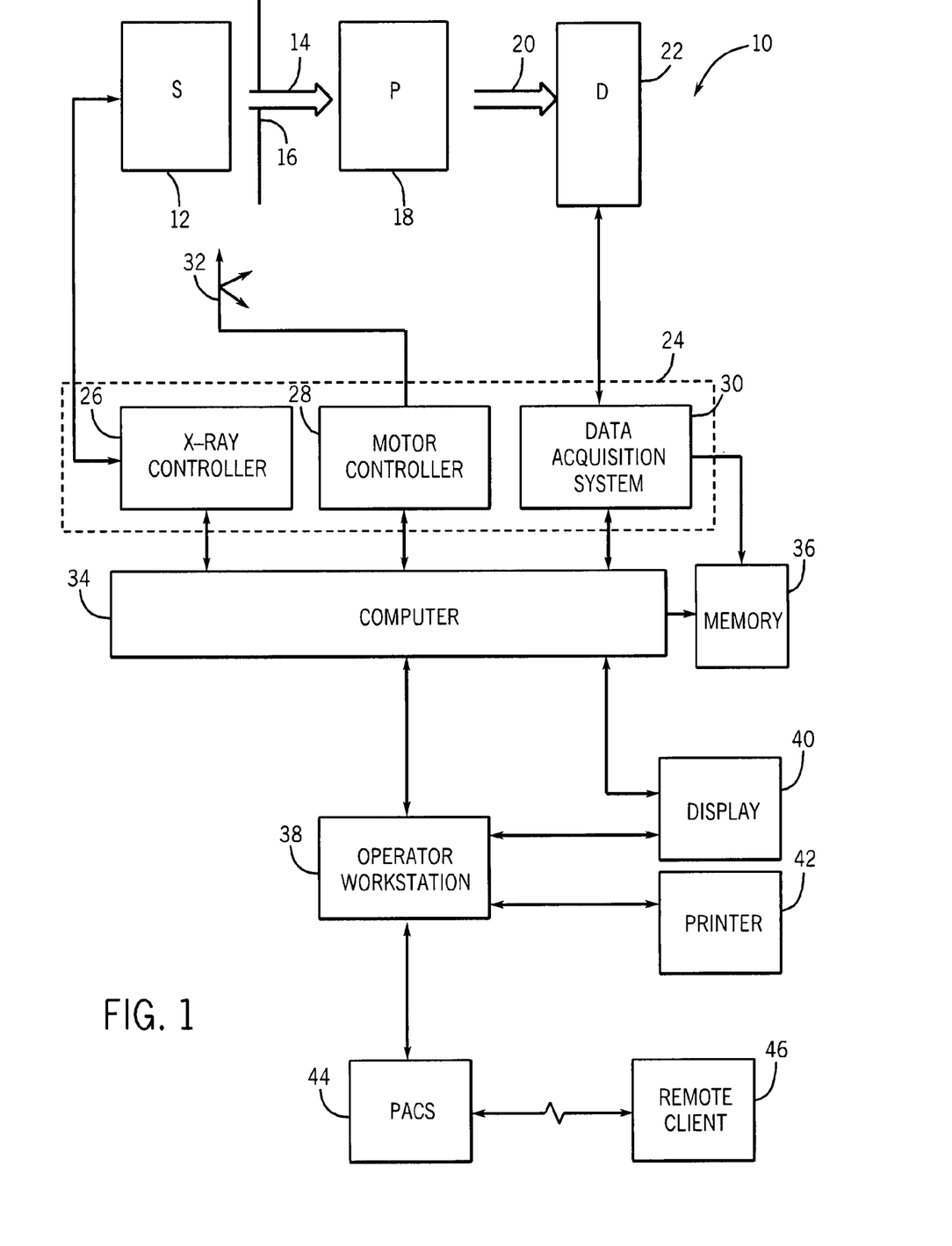
FIG. 1 is a diagrammatical view of an exemplary imaging system in the form of a tomosynthesis imaging system for use in producing processed images in accordance with aspects of the present technique.

FIG. 1 is a diagrammatical representation of an exemplary tomosynthesis system, designated generally by the reference numeral 10, for acquiring, processing and displaying tomosynthesis images, including images of various slices or slabs through a subject of interest in accordance with the present techniques. In the embodiment illustrated in FIG. 1, tomosynthesis system 10 includes a source 12 of X-ray radiation which is movable generally in a plane, or in three dimensions. In an exemplary embodiment, the X-ray source 12 includes an X-ray tube and associated support and filtering components.

A stream of radiation 14 is emitted by source 12 and passes into a region of a subject, such as a human patient 18. A collimator 16 serves to define the size and shape of the X-ray beam 14 that emerges from the X-ray source toward the subject. A portion of the radiation 20 passes through and around the subject, and impacts a detector array, represented generally by reference numeral 22. Detector elements of the array produce electrical signals that represent the intensity of the incident X-ray beam. These signals are acquired and processed to reconstruct an image of the features within the subject.

Source 12 is controlled by a system controller 24 which furnishes both power and control signals for tomosynthesis examination sequences, including position of the source 12 relative to the subject 18 and detector 22. Moreover, detector 22 is coupled to the system controller 24 which commands acquisition of the signals generated by the detector 22. The system controller 22 may also execute various signal processing and filtration functions, such as for initial adjustment of dynamic ranges, interleaving of digital image data, and so forth. In general, the system controller 24 commands operation of the imaging system to execute examination protocols and to process acquired data. In the present context, the system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, the system controller 24 includes an X-ray controller 26 which regulates generation of X-rays by the source 12. In particular, the X-ray controller 26 is configured to provide power and timing signals to the X-ray source 12. A motor controller 28 serves to control movement of a positional subsystem 32 that regulates the position and orientation of the source 12 with respect to the subject 18 and detector 22. The positional subsystem may also cause movement of the detector 22, or even the patient 18, rather than or in addition to the source 12. It should be noted that in certain configurations, the positional subsystem 32 may be eliminated, particularly where multiple addressable sources 12 are provided. In such configurations, projections may be attained through the triggering of different sources of X-ray radiation positioned differentially relative to the patient 18 and/or detector 22. Finally, in the illustration of FIG. 1, detector 22 is coupled to a data acquisition system 30 that receives data collected by read-out electronics of the detector 22. The data acquisition system 30 typically receives sampled analog signals from the detector and converts the signals to digital signals for subsequent processing by a computer 34. Such conversion, and indeed any preprocessing, may actually be performed to some degree within the detector assembly itself.

Computer 34 is typically coupled to the system controller 24. Data collected by the data acquisition system 30 is transmitted to the computer 34 and, moreover, to a memory device 36. Any suitable type of memory device, and indeed of a computer, may be adapted to the present technique, particularly processors and memory devices adapted to process and store large amounts of data produced by the system. For example, the memory device 36 may include an optical or magnetic medium, such as a hard disk, optical disk, flash memory, and so forth, suitable for storing data in accordance with the present technique or routines and algorithms for implementing some or all of the present technique on a processor-based system, such as computer 34. Moreover, computer 34 is configured to receive commands and scanning parameters from an operator via an operator workstation 38, typically equipped with a keyboard, mouse, or other input devices. An operator may control the system via these devices, and launch examinations for acquiring image data. Moreover, computer 34 is adapted to perform reconstruction of the image data as discussed in greater detail below. Where desired, other computers or workstations may perform some or all of the functions of the present technique, including post-processing of image data accessed from memory device 36 or another memory device at the imaging system location or remote from that location.

In the diagrammatical illustration of FIG. 1, a display 40 is coupled to the operator workstation 38 for viewing reconstructed images and for controlling imaging. Additionally, the image may also be printed or otherwise output in a hardcopy form via a printer 42. The operator workstation, and indeed the overall system may be coupled to large image data storage devices, such as a picture archiving and communication system (PACS) 44. The PACS 44 may be coupled to a remote client, as illustrated at reference numeral 46, such as for requesting and transmitting images and image data for remote viewing and processing as described herein. It should be further noted that the computer 34 and operator workstation 38 may be coupled to other output devices which may include standard or special-purpose computer monitors, computers and associated processing circuitry. One or more operator workstations 38 may be further linked in the system for outputting system parameters, requesting examinations, viewing images, and so forth. In general, displays, printers, workstations and similar devices supplied within the system may be local to the data acquisition components or remote from these components, such as elsewhere within an institution or in an entirely different location, being linked to the imaging system by any suitable network, such as the Internet, virtual private networks, local area networks, and so forth.

Figure 2:
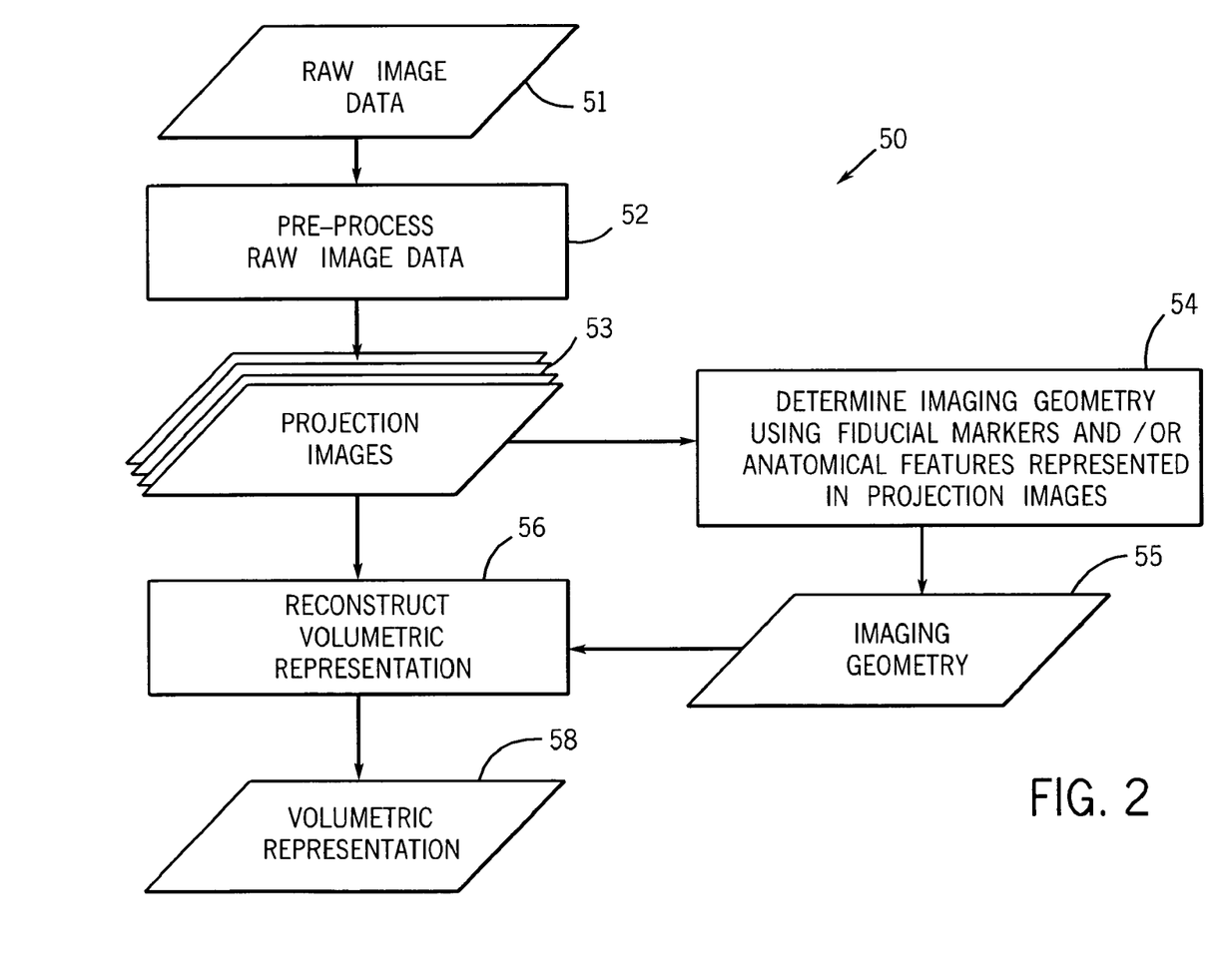
FIG. 2 is a flow chart of an exemplary embodiment of the present technique.

Referring now to FIG. 2, a flow chart illustrates an exemplary embodiment of the present technique in a process 50. Raw image data 51 may be acquired through a subject as described above in reference to FIG. 1. Included within the imaged volume are markers which may consist of anatomical features and/or fiducial markers. Anatomical features may include, for example, bones, bony structures, calcifications, implants, reference points on certain organs, interfaces between air and tissue, or vessel branching points. In one embodiment of the present technique, the whole anatomy or a comprehensive portion of the anatomy (as opposed to individual features or structures) may be used as a marker. For example, an atlas, such as a three-dimensional CT model of the imaged anatomy, may be deformed such that it matches the projection image. This matching effectively estimates two different geometric components. One component is an overall deformation of the dataset represented by the atlas to match the imaged patient anatomy. The other component, known as 3D to 2D registration, estimates the imaging geometry such that the estimated projection of the deformed atlas matches the projection image. This may be done, using suitable algorithms, for some or all projection images until there is an approximate representation of the imaged anatomy as well as a good match to the observed projection images. There may also be iterative hybrid approaches, where the first iterations are based on relatively few landmarks to obtain an estimate of the imaging geometry that is reasonably close to the true imaging geometry and additional iterations refine the obtained result by taking the comprehensive anatomy into account.

Fiducial markers are separate markers, i.e., non-anatomical markers, that have been placed within the imaged volume as references. Such fiducial markers may be spherical markers, polygonal plates, cylindrical bars, or straight wires, for example. The fiducial markers may be radiopaque or at least partially radiotransparent. These markers may, for example, be attached to the body, implanted in the body, or supported by a suitable support structure that does not move relative to the imaged anatomy. In addition, or alternatively, the fiducial markers may be rigidly attached to the detector 22 and/or the X-ray source 12. In one embodiment of the present technique, both anatomical features and fiducial markers may be used to determine the imaging geometry, while in other embodiments, only anatomical features or fiducial markers are used to determine the imaging geometry.

The raw image data 51 is processed (Block 52) to generate projection images 53. This pre-processing may include, for example, log correction of images, correction for tube-to-pixel distance, correction for the incident angle of the x-rays on the detector, and conversion of the attenuation coefficient to a line-integral or to an average attenuation along an X-ray path. In addition, pre-processing may include adjustments for dual energy imaging or for a non-planar detector. Some or all of the fiducial markers and/or anatomical features are visible in the resulting projection images 53. According to an embodiment of the present technique, not all markers may be visible in each of the projection images 53 though in other embodiments all markers are visible in each projection image 53. Additionally, some projection images 53 may not contain any visible markers, particularly where there is a well-defined relationship between imaging geometries for different subsets of the dataset or where accurate estimates of the imaging geometry of certain views may be derived from the geometry of other views. For example, in a multi-source system one source point may irradiate a portion of the imaged volume while another source point irradiates another portion of the volume. If there is a well-defined geometric relationship between the acquisition geometries of the multiple views, the imaging geometry of one view can be determined from the imaging geometry of the other view. Therefore, markers may only be visible in projection images 53 from one of the views.

The projection images 53 may then be used to determine (Block 54) the acquisition geometry 55 of the imaging system. In an exemplary embodiment of the present technique, determining the geometry consists of estimating the imaging geometry 55 based on the three-dimensional positions of the fiducial markers and/or anatomical features visible in at least some of the projection images 53. In one embodiment of the present technique, the projection images 53 are not modified, rotated, or adjusted, but rather are merely used to extract information about the imaging geometry 55. A further exemplary embodiment of the step 54 of determining the geometry is illustrated in FIG. 3.

Once the imaging geometry 55 has been determined, a volumetric representation of the imaged anatomy may be reconstructed (Block 56) from the projection images 53. This reconstruction takes into account the imaging geometry 55 when reconstructing the volumetric representation 58. The imaging geometry 55 may include the position and orientation of the X-ray source, the anatomy, and the detector, as well as other geometric information. For example, reconstruction may take into account the geometry of a non-planar detector. The projection images 53 may be processed by, for example, normalization, filtering, or linear combination of different projections. Reconstruction may account for one or more imaging geometry 55 dependent factors and may include, for example, filtered back-projection, weighted back-projection, generalized filtered back-projection, Fourier-based reconstruction, order-statistics-based reconstruction, algebraic reconstruction technique, direct algebraic reconstruction technique, or maximum-likelihood reconstruction. Reconstruction may also be based on an irregular grid, such as, for example, a pyramidal grid, a hexagonal grid, a curved coordinate system, or some coordinate system that may be suitably aligned with some anatomical structure. The resulting volumetric representation 58 of the imaged volume may then be displayed and/or analyzed or stored for later display/analysis.

Figure 3:
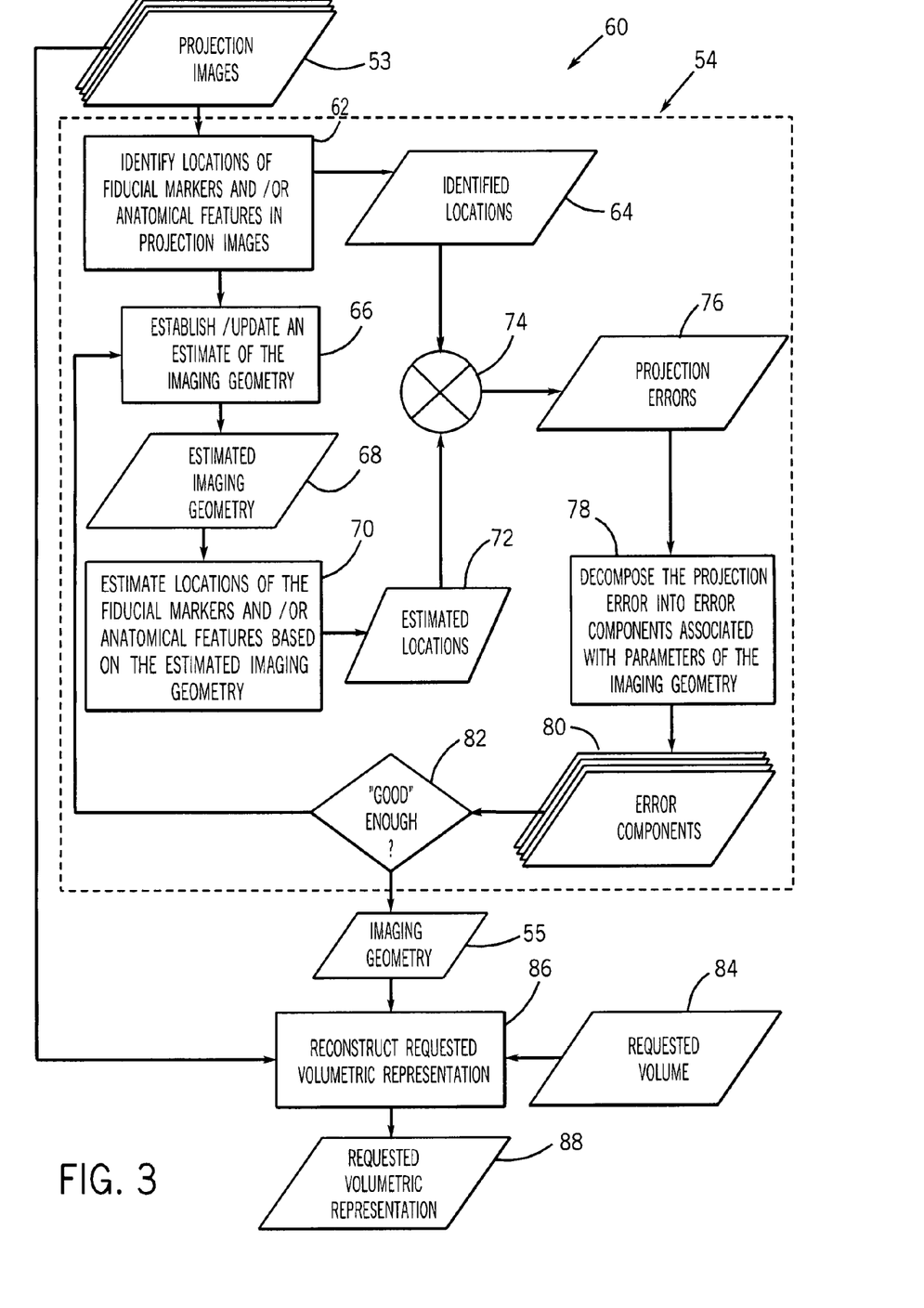
FIG. 3 is a flow chart of a further embodiment of the present technique.

Turning to FIG. 3, a flow chart illustrates an exemplary embodiment of an aspect of the present technique in a process 60 in which an exemplary embodiment of the geometry determination 54 is depicted. The projection images 53 may be generated from pre-processing the raw image data as discussed above in reference to FIG. 2. Locations 64 of the fiducial markers and/or anatomical features may be identified (Block 62) in some or all of the projection images 53. This identification may be automatic, manual, or semi-automatic, that is, with some user interaction. Automatic identification may, for example, use approaches from general image processing, medical image processing, or computer vision. For the identification and localization of anatomical markers, general anatomical models, anatomical atlases, and algorithms that leverage prior anatomical knowledge may be used. If the set of markers is general enough, not all markers need to be identified and located in each image, that is, a subset may be sufficient. In some cases, not all markers may be visible or identifiable in each projection image.

Next, an estimate 68 of the imaging geometry may be established (Block 66). In some embodiments of the present technique, the imaging geometry may be partially known for at least some of the projection images 53. That is, for example, the imaging system configuration may be such that during the image acquisition there was a fixed source-to-detector distance or a fixed principal point, such as a projection of a focal spot onto the detector plane. Alternatively, during the acquisition the detector may be stationary relative to the imaged subject or may travel along a well-defined circular trajectory, and only the angular position along this trajectory may need to be determined. In other embodiments of the present technique, the relative position of the imaged markers may be at least partially known. That is, there may be prior knowledge of the distance between some or all of the markers, or there may be prior knowledge of the angles between pairs of lines through three or more markers. In one embodiment of the present technique, fiducial markers may be used such that their three-dimensional positions are fully known, such as with the use of a well-defined calibration phantom, in which case the imaging geometry 55 may be estimated from the information extracted from the projection images 53. According to another embodiment of the present technique, the three-dimensional position of the markers may be estimated. This estimation may include an iterative process in which an estimate of the three-dimensional marker positions is computed and the imaging geometry 55 is then computed such that the predicted location of the markers in the projection images 53 best matches the detected marker locations in the projection images 53.

From the estimated imaging geometry 68, the estimated locations 72 of the fiducial markers and/or anatomical features in the projection images 53 may be determined (Block 70). In some embodiments, the identified locations 64 in conjunction with knowledge of the associated projection images 53 may be used to actually estimate the three-dimensional locations of the markers as part of estimating the imaging geometry 68. In this case, estimation of the imaging geometry 68 may be performed in conjunction with estimating the three-dimensional locations of the markers, or these operations may be performed as separate steps. The step 70 of estimating the three-dimensional locations of the markers may not be performed in every iteration. Once the estimated locations 72 have been determined, they may then be compared to the previously-identified locations 64. For each marker, projection errors 76 are calculated (Block 74) based upon the difference between the identified locations 64 and the estimated locations 72. These projection errors 76 may be decomposed (Block 78) into two or more error components 80, at least one of which corresponds to a respective geometric parameter of the imaging geometry 55. Geometric parameters of the imaging geometry may include, for example, the three parameters describing the three-dimensional position of the source 12 (i.e., translation in both horizontal directions and in the vertical direction relative to the detector), the three parameters describing the three-dimensional position of the detector 22 (i.e., translation in both horizontal directions and in the vertical direction), and the three parameters describing the three-dimensional orientation of the detector 22 (i.e., in-plane rotation and tilt in two directions).

The error components 80 may be analyzed (Block 82) to determine whether the estimated imaging geometry 68 is adequate, that is, whether there would be no significant image quality degradation due to geometric imperfections. If the error components are too large, one or more geometric parameters may be updated (Block 66) to produce a new estimated imaging geometry 68 based on the projection images 53 and the error components 80. In some cases, good image quality may be achieved without having determined a very accurate representation of the three-dimensional imaging geometry 55. In such cases, there has generally been a good alignment of the markers' estimated locations 72 with the identified locations 64 based on the estimated imaging geometry 68, which is sufficient for good image quality in the reconstructed dataset. In an exemplary embodiment of the present technique where the imaging geometry 55 is partially known, this knowledge may be used to constrain iterative updates of the estimated imaging geometry 68. In another embodiment of the present technique where the relative positions of the markers are at least partially known, this knowledge may also be used to constrain iterative updates of the estimated three-dimensional positions of the markers. These constraints may not be applied in every iteration. Those of ordinary skill in the art will appreciate that techniques such as these and those described in U.S. application Ser. No. 11/289,346, titled "Method and Device for Geometry Analysis and Calibration of Volumetric Imaging Systems" and filed on Nov. 29, 2005, by Bernhard Claus, herein incorporated by reference in its entirety, may also be employed.

The operations in Blocks 66 through 82 may be repeated as many times as necessary to achieve an adequate imaging geometry 55. In each iteration, one or more geometric parameters may be adjusted to update the estimated imaging geometry 68. In addition, different parameters may be adjusted in different iterations. Once the error components 80 are sufficiently small, the imaging geometry 55 may be used to reconstruct the projection images 53 using techniques similar or identical to that of reconstruction 56, discussed above in reference to FIG. 2 (Block 86). According to an exemplary embodiment of the present technique, some or all of the imaged volume may be reconstructed. That is, a user may input a requested volume 84 that may include only that volume or sub-volume in which the user is particularly interested. A configurable volumetric representation 88 of the imaged subject may then be analyzed or stored for later use.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for three-dimensional imaging in a non-calibrated geometry, wherein the method is performed using a processor or computer, the method comprising:
   acquiring a plurality of projection images through an imaging volume;
   estimating an imaging geometry using at least one of fiducial markers or anatomical features or regions represented in the projection images, wherein estimating the imaging geometry comprises:
      identifying locations of the fiducial markers or anatomical features in some or all of the plurality of projection images;
      establishing an estimate of the imaging geometry;
      estimating locations of the fiducial markers or anatomical features in the projection images based on the estimate of the imaging geometry;
      computing a projection error between the estimated locations of the fiducial markers or anatomical features and the identified locations of the respective fiducial markers or anatomical features for at least one projection image; and
      updating the estimated imaging geometry based on the projection error; and
   reconstructing a configurable volumetric representation of some or all of the imaging volume using the estimated imaging geometry, wherein the act of reconstructing accounts for one or more geometry dependent factors.

2. The method of claim 1, wherein estimating the imaging geometry comprises estimating locations of at least some of the fiducial markers or anatomical features in at least one of the respective projection images or in a respective three-dimensional volume.

3. The method of claim 1, comprising constraining the estimated imaging geometry based on a partially known imaging geometry.

4. The method of claim 1, comprising constraining the estimated imaging geometry based on partially known relative positions of the fiducial markers or anatomical features.

5. The method of claim 1, wherein not all fiducial markers or anatomical features are represented in every projection image.

6. The method of claim 1, wherein updating the estimated imaging geometry comprises:
decomposing the computed projection error into one or more error components corresponding to respective parameters of the imaging geometry; and
updating at least one parameter of the estimated imaging geometry based on the one or more error components.

7. The method of claim 1, comprising iterating the steps of establishing an estimate of the imaging geometry, computing the projection error, and updating the estimated imaging geometry.

8. A method for three-dimensional imaging in a non-calibrated geometry, wherein the method is performed using a processor or computer, the method comprising:
acquiring a plurality of projection images through an imaging volume;
estimating an imaging geometry using one or more anatomical features represented in the projection images, wherein estimating the imaging geometry comprises:
identifying locations of the anatomical features in some or all of the plurality of projection images;
establishing an estimate of the imaging geometry;
estimating locations of the anatomical features based on the estimate of the imaging geometry;
computing a projection error between the estimated locations of the anatomical features and the identified locations of the respective anatomical features for at least one projection image; and
updating the estimated imaging geometry based on the projection error; and
reconstructing a volumetric representation of some or all of the imaging volume using the established imaging geometry.

9. The method of claim 8, wherein estimating the imaging geometry comprises identifying suitable anatomical features from at least one of general anatomical models, anatomical atlases, or at least one of the projection images.

10. The method of claim 8, wherein updating the estimated imaging geometry comprises:
decomposing the computed projection error into one or more error components corresponding to respective parameters of the imaging geometry; and
updating at least one parameter of the estimated imaging geometry based on the one or more error components.

11. The method of claim 8, comprising iterating the steps of establishing an estimate of the imaging geometry, computing the projection error, and updating the estimated imaging geometry.

12. An image processing system comprising:
a memory device storing executable routines, which when executed, perform the acts of: identifying locations of one or more fiducial markers or anatomical features in some or all of a plurality of projection images; establishing an estimate of an imaging geometry used to acquire the plurality of projection images; estimating locations of the fiducial markers or anatomical features in the projection images based on the estimate of the imaging geometry; computing a projection error between the estimated locations of the fiducial markers or anatomical features and the identified locations of the respective fiducial markers or anatomical features for at least one projection image; updating the estimated imaging geometry based on the projection error; and reconstructing a configurable volumetric representation of some or all of the imaging volume using the estimated imaging geometry;
a computer configured to execute the executable routines stored on the memory device; and
a display on which the configurable volumetric representation is displayed.

13. The image processing system of claim 12, wherein the memory device stores at least one of the plurality of projection images or the configurable volumetric representation.

14. An image processing system comprising:
a memory device storing executable routines, which when executed, perform the acts of: identifying locations of anatomical features in some or all of a plurality of projection images; establishing an estimate of an imaging geometry used to acquire the plurality of projection images; estimating locations of the anatomical features based on the estimate of the imaging geometry; computing a projection error between the estimated locations of the anatomical features and the identified locations of the respective anatomical features for at least one projection image; updating the estimated imaging geometry based on the projection error; and reconstructing a volumetric representation of some or all of the imaging volume using the estimated imaging geometry;
a computer configured to execute the executable routines stored on the memory device; and
a display on which the volumetric representation is displayed.

15. The image processing system of claim 14, wherein the memory device stores at least one of the plurality of projection images or the volumetric representation.

16. One or more non-transitory computer readable media, comprising code executable to perform the acts of:
estimating an imaging geometry using at least one of fiducial markers or anatomical features represented in a plurality of projection images acquired through an imaging volume, wherein estimating the imaging geometry comprises:
identifying locations of the fiducial markers or anatomical features in some or all of the plurality of projection images;
establishing an estimate of the imaging geometry;
establishing estimated locations of the fiducial markers or anatomical features based on the estimate of the imaging geometry;
computing a projection error between the estimated locations of the fiducial markers or anatomical features and the identified locations of the respective fiducial markers or anatomical features for at least one projection image; and
updating the estimated imaging geometry based on the projection error; and
reconstructing a configurable volumetric representation of some or all of the imaging volume using the estimated imaging geometry, wherein the act of reconstructing accounts for one or more geometry dependent factors.

17. The non-transitory computer readable media of claim 16, comprising code executable to perform the act of iterating the steps of establishing an estimate of the imaging geometry, computing the projection error, and updating the estimated imaging geometry.

18. The non-transitory computer readable media of claim 16, wherein updating the estimated imaging geometry comprises:
   decomposing the computed projection error into one or more error components corresponding to respective parameters of the imaging geometry; and
   updating at least one parameter of the estimated imaging geometry based on the one or more error components.

19. The non-transitory computer readable media of claim 18, comprising code executable to perform the act of iterating the steps of establishing an estimate of the imaging geometry, computing the projection error, decomposing the computed projection error, and updating the at least one parameter of the estimated imaging geometry, wherein updating the at least one parameter comprises selectively updating one or more parameters in each iteration.

20. One or more non-transitory computer readable media, comprising code executable to perform the acts of:
   estimating an imaging geometry using anatomical features represented in a plurality of projection images acquired through an imaging volume, wherein estimating the imaging geometry comprises:
      identifying locations of the anatomical features in some or all of the plurality of projection images;
      establishing an estimate of the imaging geometry;
      establishing estimated locations of the anatomical features based on the estimate of the imaging geometry;
      computing a projection error between the estimated locations of the anatomical features and the identified locations of the respective anatomical features for at least one projection image; and
      updating the estimated imaging geometry based on the projection error; and
   reconstructing a volumetric representation of some or all of the imaging volume using the estimated imaging geometry.

21. The non-transitory computer readable media of claim 20, comprising code executable to perform the act of iterating the steps of establishing an estimate of the imaging geometry, computing the projection error, and updating the estimated imaging geometry.

22. The non-transitory computer readable media of claim 20, wherein updating the estimated imaging geometry comprises:
   decomposing the computed projection error into one or more error components corresponding to respective parameters of the imaging geometry; and
   updating at least one parameter of the estimated imaging geometry based on the one or more error components.

23. The non-transitory computer readable media of claim 22, comprising code executable to perform the act of iterating the steps of establishing an estimate of the imaging geometry, computing the projection error, decomposing the computed projection error, and updating the at least one parameter of the estimated imaging geometry, wherein updating the at least one parameter comprises selectively updating one or more parameters in each iteration.

* * * * *